US012605094B2

(12) United States Patent
Oh et al.

(10) Patent No.: US 12,605,094 B2
(45) Date of Patent: Apr. 21, 2026

(54) CLOSED TYPE ARTERIAL BLOOD COLLECTION APPARATUS

(71) Applicant: MUNE CO., LTD., Seoul (KR)

(72) Inventors: Kwang Bin Oh, Seoul (KR); You Hwa Kim, Chungcheongnam-do (KR); Jae Hak Jeong, Gyeonggi-do (KR); Ju Han Kim, Gyeonggi-do (KR); Dong Kyu Park, Gyeonggi-do (KR); In Hwa Kim, Gyeonggi-do (KR); Nam Yeong Kim, Busan (KR); Jae Myeong Lee, Seoul (KR)

(73) Assignee: MUNE CO., LTD., Seoul (KR)

( * ) Notice: Subject to any disclaimer, the term of this patent is extended or adjusted under 35 U.S.C. 154(b) by 481 days.

(21) Appl. No.: 18/270,088

(22) PCT Filed: Dec. 28, 2022

(86) PCT No.: PCT/KR2022/021450
§ 371 (c)(1),
(2) Date: Jun. 28, 2023

(87) PCT Pub. No.: WO2024/143595
PCT Pub. Date: Jul. 4, 2024

(65) Prior Publication Data
US 2024/0398296 A1     Dec. 5, 2024

(51) Int. Cl.
A61B 5/15 (2006.01)

(52) U.S. Cl.
CPC .... *A61B 5/15003* (2013.01); *A61B 5/150221* (2013.01); *A61B 5/150229* (2013.01); *A61B*

*5/150824* (2013.01); *A61B 5/150992* (2013.01); *A61B 2562/00* (2013.01)

(58) Field of Classification Search
CPC ....... A61B 5/024; A61B 5/15; A61B 5/15003; A61B 5/150221; A61B 5/150229; A61B 5/150824; A61B 5/150992; A61B 5/153; A61B 2562/00; A61M 5/44
USPC ........................................................ 600/581
See application file for complete search history.

(56) References Cited

U.S. PATENT DOCUMENTS

2007/0191716 A1 * 8/2007 Goldberger ...... A61B 5/150992
600/481

* cited by examiner

*Primary Examiner* — Alex M Valvis
*Assistant Examiner* — Anna Roberts
(74) *Attorney, Agent, or Firm* — Mendelsohn Dunleavy, P.C.

(57) ABSTRACT

A closed type arterial blood collection apparatus is disclosed. The closed type arterial blood collection apparatus includes a saline bag provided at a lower end thereof with a first port and a second port, an A line configured to connect an arterial blood vessel of a patient to the first port, a first three-way valve configured to open and close the A line, a blood collection unit configured to collect arterial blood through the first three-way valve, a second three-way valve provided between the first three-way valve and the first port, the second three-way valve being configured to open and close the A line, a guide tube configured to connect the second three-way valve to the second port, and a fluid conveying means configured to convey a fluid in the guide tube when the A line and the guide tube are connected to each other.

5 Claims, 10 Drawing Sheets

CLOSED TYPE ARTERIAL BLOOD COLLECTION APPARATUS

TECHNICAL FIELD

The present invention relates to an arterial blood collection apparatus, and more particularly to a closed type arterial blood collection apparatus capable of withdrawing initial blood in an arterial line diluted with a saline solution, collecting a required amount of internal blood, and transfusing the initial blood back into a body, thereby minimizing loss of patient blood at the time of arterial blood collection.

BACKGROUND ART

An arterial line (A line) is a tool configured to observe hemodynamic status of a patient, such as blood pressure or pulsation, and to collect arterial blood. The arterial line is constituted by a catheter configured to be inserted into the artery, a tube connected to a saline bag, and a three-way valve installed at the tube. In addition, a transducer configured to convert pulsation into an electrical signal is connected to the tube. The electrical signal generated through the transducer may be transmitted to a monitor, and a doctor or a nurse may check the status of the patient through the monitor.

For patients in an intensive care unit (ICU) on whom the arterial line is put in order to monitor arterial pressure, internal blood is collected using the arterial line when a test, such as Arterial blood gas analysis, Complete blood count, or Blood Chemistry Examination, is performed.

In general, when blood is collected through the arterial line, about 5 cc of initial blood that is initially collected is thrown away, and internal blood is taken. The initial blood is blood collected when blood collection is started, and the internal blood is blood after the initial blood. The reason that the initial blood is thrown away is that the initial blood is mixed with heparin or is diluted with a saline solution without heparin, whereby it is not possible to obtain an accurate test result value.

Blood is frequently collected from a patient in the intensive care unit (ICU) every day, whereby the patient may become anemic. Arterial blood gas analysis may be performed at least once per day to as much as every hour or dozens of times per day depending on the state of the patient. As a result, the amount of blood collected from a critical patient per day ranges from about 26 ml to as much as over 478 ml. Since initial blood is thrown away at every test, the actual amount of blood that the patient loses is greater than the above-specified amount. A report says that the moderate to severe anemia incidence rate at every collection of 50 cc of blood is 18% or more and that 97% of inpatients suffer from anemia due to frequent blood collection.

A VAMP manufactured by Edwards Lifesciences is known as a solution to the above problems with blood collection. The VAMP (hereinafter referred to as a conventional product) is a blood collection apparatus that stores initial blood in an external reservoir without being thrown away, takes internal blood, and transfuses the initial blood back into a body.

However, the conventional product has a problem in that thrombus is generated in the initial blood. This is because pooled, stationary blood property of coagulating quickly. Particularly, when the initial blood is introduced into the reservoir, the sectional area of the initial blood is greatly increased. In addition, when the initial blood received in the reservoir is transfused into back the body of a patient, pressure is applied to the initial blood and the patient's circulatory system, whereby a possibility of thrombus generation is further increased.

Also, in the conventional product, the reservoir is installed between a catheter and a transducer, whereby a damping phenomenon occurs in arterial blood pressure monitoring performed by the transducer. The reservoir disturbs a pulse signal transmitted from an arterial blood vessel to the transducer. In other words, the reservoir acts as an obstacle to the pulse signal, reducing pulse reading accuracy.

DISCLOSURE

Technical Problem

The present invention has been made in view of the above problems, and it is an object of the present invention to provide a closed type arterial blood collection apparatus that does not generate thrombus, whereby safe use thereof is possible, that enables a transducer to be accurately operated, and that can be used in a state of being connected to an existing blood collection apparatus.

Technical Solution

In order to accomplish the above object, a closed type arterial blood collection apparatus according to the present invention includes a saline bag configured to receive a saline solution, the saline bag being provided at a lower end thereof with a first port and a second port, an A line configured to connect an arterial blood vessel of a patient to the first port, the A line being filled with the saline solution in the saline bag, a first three-way valve configured to open and close the A line in a state of being mounted on the A line, a blood collection unit configured to collect arterial blood through the first three-way valve when the first three-way valve closes the A line, a second three-way valve provided between the first three-way valve and the first port, the second three-way valve being configured to open and close the A line, a guide tube configured to connect the second three-way valve to the second port, the guide tube being filled with the saline solution in the saline bag, and a fluid conveying means configured to convey a fluid in the guide tube to the saline bag when the A line and the guide tube are connected to each other as the result of operation of the second three-way valve.

A transducer configured to convert a pulse signal of the artery of the patient transmitted through the saline solution used as a medium into an electrical signal and to transmit the electrical signal to an external patient monitor may be mounted on the A line.

The A line may include a catheter having a blood collection needle, the catheter being connected to the first three-way valve, a proximal tube configured to connect the first three-way valve and the second three-way valve to each other, and a distal tube configured to connect the second three-way valve and the first port to each other.

The fluid conveying means may include a pump configured to press an outer circumferential surface of the guide tube in a longitudinal direction thereof in order to push the blood in the guide tube in the longitudinal direction of the guide tube such that the blood is moved in the longitudinal direction of the guide tube.

A check valve configured to prevent the fluid introduced into the guide tube from the proximal tube via the second three-way valve from being introduced into the second port may be installed between the pump and the second port.

A pressure accumulation unit configured to accumulate inner pressure of the guide tube increasing as the result of operation of the pump may be further installed between the pump and the check valve.

The pressure accumulation unit may have a pressure resistant cylinder configured to receive compressible gas and the saline solution and to indicate the level of the saline solution based on change in inner pressure to the outside.

The pressure accumulation unit may further have a pressure sensor configured to sense the inner pressure of the pressure resistant cylinder, a water level sensor configured to sense the level of the saline solution, a control module connected to the pressure sensor and the water level sensor, the control module being configured to output a signal when change in each of the inner pressure of the pressure resistant cylinder and the level of the saline solution exceeds a predetermined range, and a pressure lamp and a water level lamp configured to be operated under control of the control module.

A temperature maintenance unit configured to maintain the temperature of the fluid in the A line or the guide tube at the temperature of the patient may be installed.

The temperature maintenance unit may include a constant temperature jacket configured to wrap around the A line or the guide tube, a temperature controller configured to control the temperature of the constant temperature jacket, and an indication lamp configured to be turned on when the temperature of heat generated by the constant temperature jacket is within a normal range.

Advantageous Effects

As is apparent from the above description, no thrombus is generated in initial blood collected by a closed type arterial blood collection apparatus according to the present invention and no residual blood remains in the closed type arterial blood collection apparatus after flushing, whereby safe use of the closed type arterial blood collection apparatus is possible.

In addition, no obstacle that disturbs a pulse signal is present between an arterial blood vessel of a patient and a transducer, whereby accurate monitoring is possible.

Furthermore, the closed type arterial blood collection apparatus according to the present invention is used in a state of being easily connected to an existing blood collection apparatus, whereby utilization of the closed type arterial blood collection apparatus is high.

BEST MODE

Hereinafter, an embodiment of the present invention will be described in detail with reference to the accompanying drawings.

A closed type arterial blood collection apparatus according to the present invention, which is mainly used in an intensive care unit of a hospital, minimizes anemia of patients due to frequent blood collection. The basic principle by which anemia is prevented is to transfuse initial blood at the time of blood collection (thrown away so far) into the body of a patient again. The "initial blood" is blood that abuts a saline solution containing heparin. That is, the initial blood is blood that is diluted by a saline solution and is mixed with heparin and cannot be used to accurately test blood.

The closed type arterial blood collection apparatus according to the present invention basically includes a saline bag configured to receive a saline solution, the saline bag being provided at a lower end thereof with a first port and a second port, an A line configured to connect an arterial blood vessel of a patient to the first port, the A line being filled with the saline solution in the saline bag, a first three-way valve configured to open and close the A line in a state of being mounted on the A line, a blood collection unit configured to collect arterial blood through the first three-way valve when the first three-way valve closes the A line, a second three-way valve provided between the first three-way valve and the first port, the second three-way valve being configured to open and close the A line, a guide tube configured to connect the second three-way valve to the second port, the guide tube being filled with the saline solution in the saline bag, and a fluid conveying means configured to convey a fluid in the guide tube when the A line and the guide tube are connected to each other as the result of operation of the second three-way valve.

Figure 1:
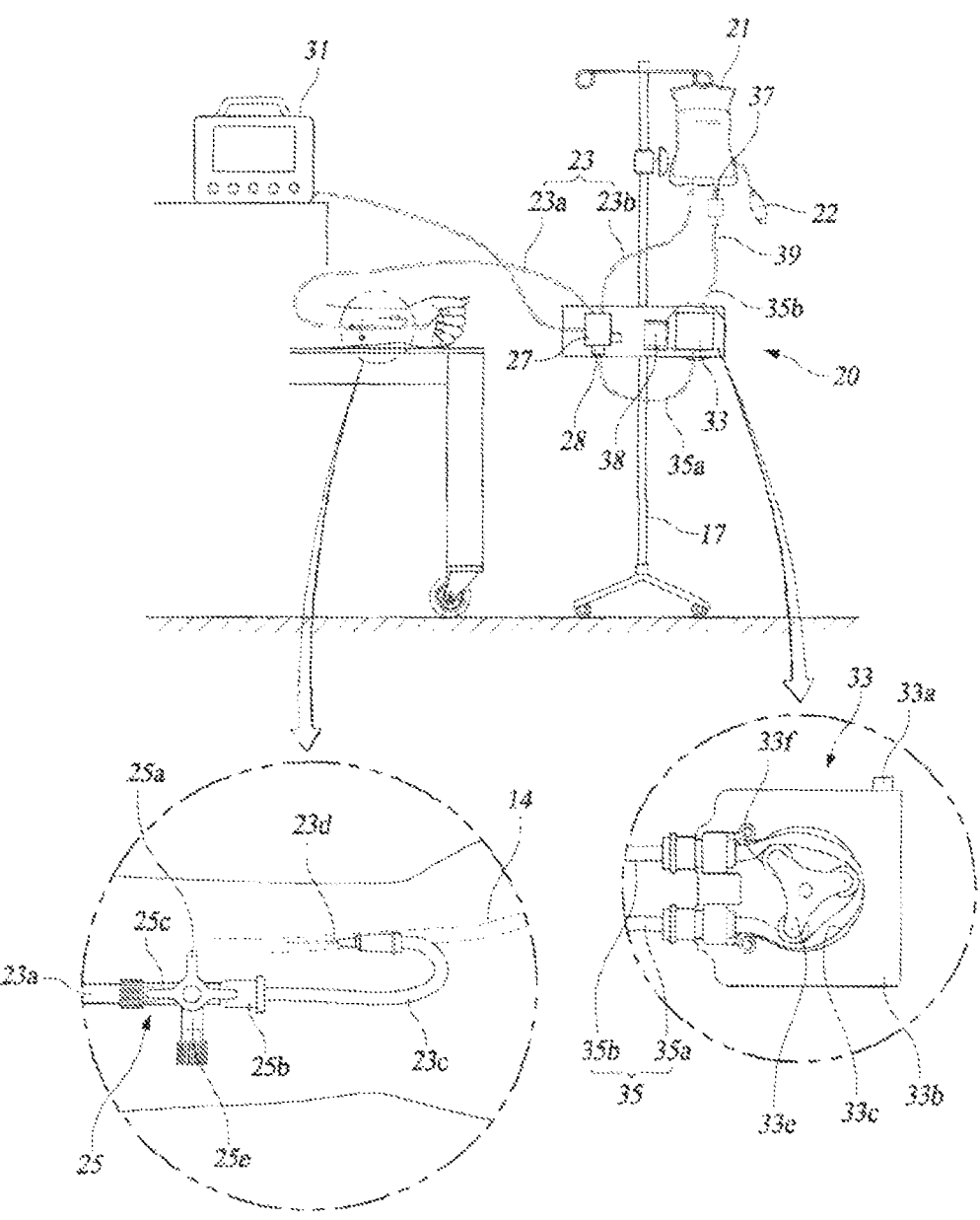
FIG. 1 is a view showing the construction of a closed type arterial blood collection apparatus according to an embodiment of the present invention.
Figure 2:
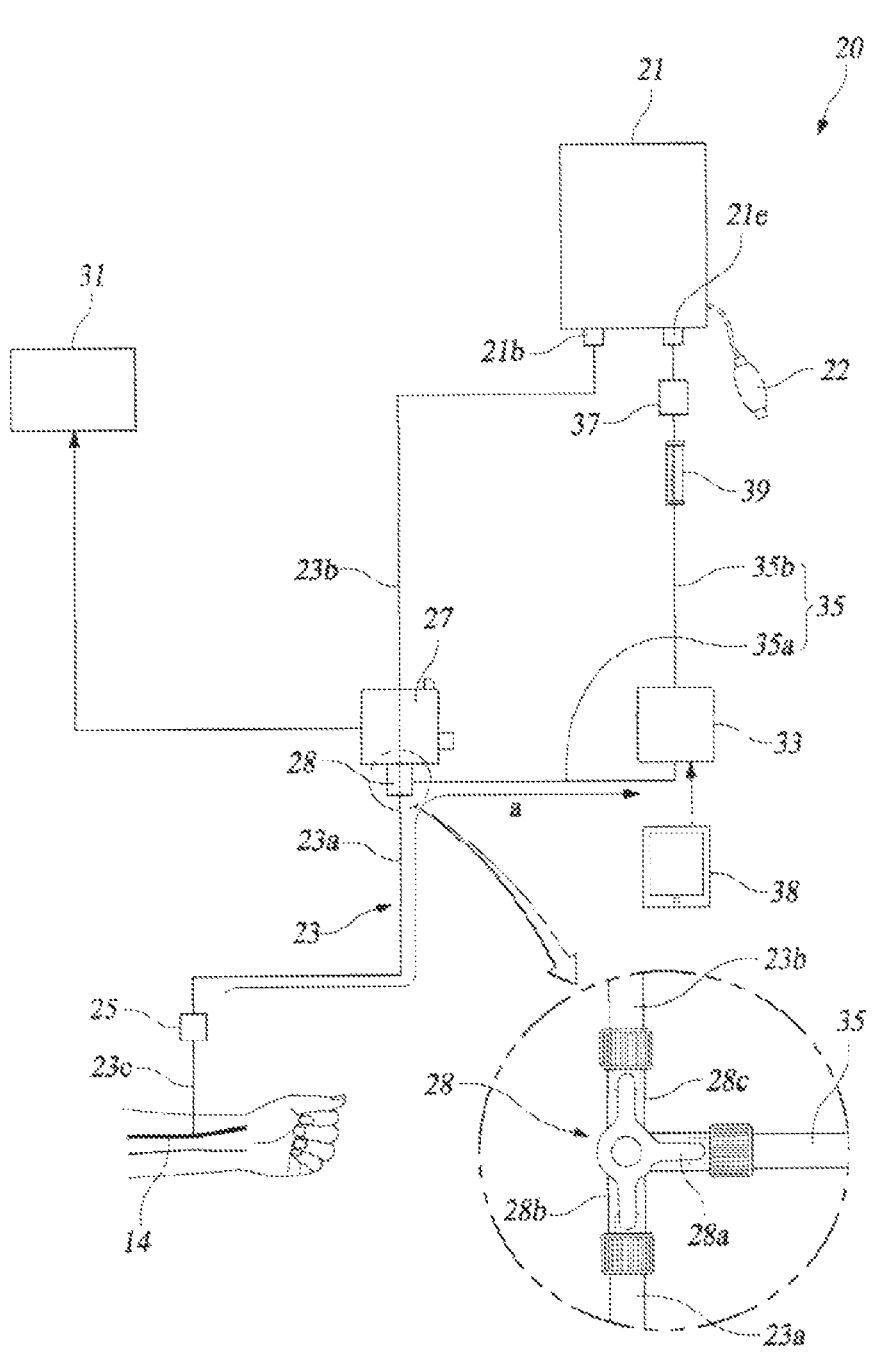
FIG. 2 is a view showing the connection relationship between respective units of the blood collection apparatus shown in FIG. 1.

FIG. 1 is a view schematically showing the construction of a closed type arterial blood collection apparatus 20 according to an embodiment of the present invention, and FIG. 2 is a view showing the connection relationship between respective units of the blood collection apparatus shown in FIG. 1.

As shown, the closed type arterial blood collection apparatus 20 according to the present embodiment includes a saline bag 21, an A line 23, a first three-way valve 25, a blood collection unit, a second three-way valve 28, a guide tube 35, a fluid conveying means, a touch panel 38, a check valve 37, and a pressure accumulation chamber 39.

The saline bag 21, which is a vinyl bag having a saline solution received therein, is provided at a lower end thereof with a first port 21b and a second port 21e. The interior of the saline bag 21 is maintained at a pressure of about 300 mmHg. In addition, a manual compressor 22 is connected to the saline bag 21 in order to adjust the inner pressure of the saline bag 21, as needed. The manual compressor 22 is a general compression means that a user operates by hand. In addition, the saline solution in the saline bag 21 includes heparin. Heparin is injected into the saline bag in advance through an A port or a B port. In the same manner as general saline solution bags, the saline bag 21 is held at an upper end of a pole 17.

The A line 23 provides a passage configured to connect an arterial blood vessel 14 of a patient to the first port 21b. The interior of the passage of the A line 23 is filled with the saline solution in the saline bag 21, and water pressure of the saline solution and the internal pressure of the saline bag 21 are transferred to a lower end of the A line 23, i.e. an end of a catheter 23c.

The A line 23 has a catheter 23c, a proximal tube 23a, and a distal tube 23b. The catheter 23c is a tube having a blood collection needle 23d provided at one end thereof, and the other end of the catheter is connected to the first three-way valve 25. When the blood collection needle 23d penetrates the arterial blood vessel 14, arterial blood flows into the catheter 23c through the blood collection needle 23d.

The proximal tube 23a is a flexible tube configured to connect the first three-way valve 25 and the second three-way valve 28 to each other, and the distal tube 23b is a flexible tube configured to connect the second three-way valve and the first port 21b to each other. The proximal tube 23a communicates with the catheter 23c through the first three-way valve 25, and the distal tube 23b communicates with the proximal tube 23a through the second three-way valve 28.

The saline solution in the saline bag 21 may reach the arterial blood vessel 14 via the first port 21b, the distal tube 23b, the second three-way valve 28, the proximal tube 23a, the first three-way valve 25, and the catheter 23c. The length of each of the proximal tube 23a and the distal tube 23b may be freely changed, as needed.

The first three-way valve 25 is a three-way valve configured to open and close the passage of the A line in a state of being mounted on the A line. When the A line is opened, the saline solution or the blood may move in the A line. When the A line is closed, a movement route of the saline solution or the blood is blocked.

As shown in an enlarged scale in FIG. 1, the first three-way valve 25 has a catheter fixing port 25b, a tube connection port 25c, a blood collection port 25e, and a switching lever 25a.

Figure 5:
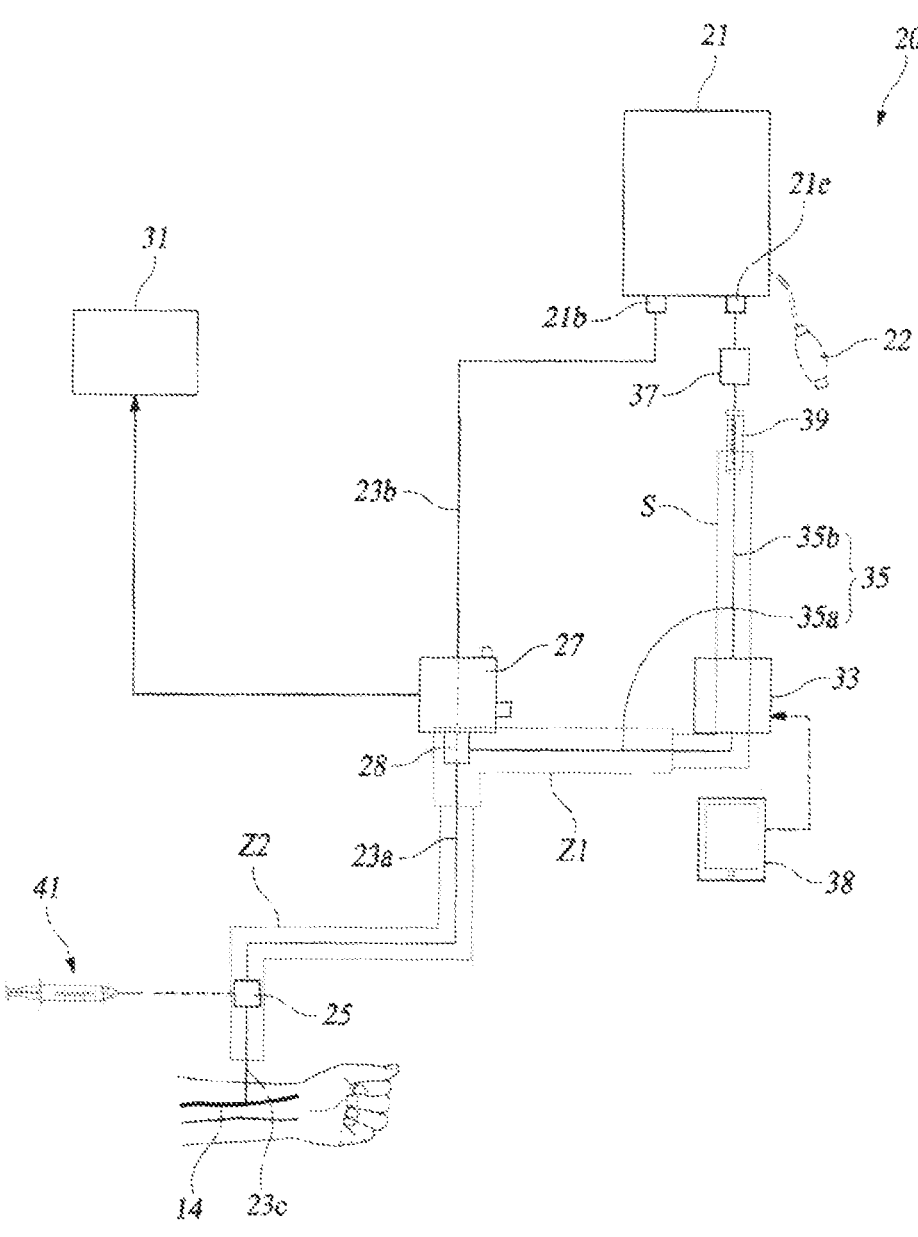

The catheter fixing port 25b has a hole configured to allow an end of the catheter 23c to be fixed thereto, and the tube connection port 25c is a passage configured to allow one end of the proximal tube 23a to be coupled thereto. In addition, the blood collection port 25e is a passage configured to allow the blood in the catheter 23c to be collected therethrough. The blood collection unit, i.e. a blood collection syringe 41 (FIG. 5), may be connected to the blood collection port 25e in order to perform blood collection.

The blood collection unit, which is configured to collect arterial blood through the blood collection port 25e of the first three-way valve 25 when the first three-way valve closes the A line 23, includes a blood collection syringe 41. A doctor or a nurse rotates the switching lever 25a, connects the blood collection syringe 41 to the blood collection port 25e, and performs blood collection.

The switching lever 25a is a manual lever configured to switch between flow channels in the first three-way valve 25. As previously described, the switching lever 25a may be rotated in order to connect the catheter 23c and the proximal tube 23a to each other and at the same time to block the blood collection port 25e or in order to block the catheter 23c and the proximal tube 23a and allow the catheter 23c and the blood collection port 25e to communicate with each other therethrough.

The second three-way valve 28 is a three-way valve having the same construction as the first three-way valve 25. The second three-way valve 28 is provided with first, second, and third ports 28b, 28c, and 28d and a switching lever 28a. The first port 28b is connected to the proximal tube 23a, the second port 28c is connected to the distal tube 23b, and the third port 28d is connected to the guide tube 35.

The switching lever 28a switches between flow channels in the second three-way valve 28 in order to connect the proximal tube 23a and the distal tube 23b to each other and at the same time to block the guide tube 35 or in order to connect the proximal tube 23a and the guide tube 35 to each other and at the same time to block the distal tube 23b. The second three-way valve 28 may be integrally formed with a transducer 27. Alternatively the second three-way valve 28 and the transducer 27 may be separately formed and installed.

The transducer 27 converts a pulse signal of an artery of the patient received through the saline solution used as a medium into an electrical signal and transmits the converted electrical signal to an external patient monitor 31. The structure and function of the transducer 27 are known, and therefore a description thereof will be omitted.

Meanwhile, the guide tube 35 is a flexible tube having one end connected to the third port 28d of the second three-way valve 28 and the other end connected to the second port 21e of the saline bag 21. The interior of a passage of the guide tube 35 is filled with the saline solution in the saline bag. The length of the guide tube 35 may also be freely changed, as needed.

The guide tube 35 is a single body tube. For convenience of description, the guide tube may be divided into a first guide tube portion 35a and a second guide tube portion 35b based on a pump 33. The first guide tube portion 35a is a part configured to connect the second three-way valve 28 and the pump 33 to each other, and the second guide tube portion 35b is a part configured to connect the pump 33 and the second port 21e to each other. The length of each of the first guide tube portion 35a and the second guide tube portion 35b may also be changed.

The pump 33, the check valve 37, and the pressure accumulation chamber 39 are installed on the guide tube 35.

The pump 33 is a fluid conveying means configured to convey the fluid (the saline solution or the initial blood) in a direction indicated by arrow a when the proximal tube 23a and the guide tube 35 are connected to each other as the result of operation of the second three-way valve 28.

The pump 33 is a peristaltic pump configured to press an outer circumferential surface of the guide tube 35 in a longitudinal direction thereof in order to push the fluid in the guide tube in the longitudinal direction of the guide tube such that the fluid is moved in the longitudinal direction of the guide tube. The pump 33 includes a housing 33b configured to provide an outer circumferential surface 33c for support having predetermined curvature, a rotor 33e mounted in the housing 33b, the rotor being configured to be rotated in both directions, a motor (not shown) configured to rotate the rotor 33e, and a plurality of pressing rolls 33f fixed to an end of the rotor 33e in a radial direction thereof.

The guide tube 35 is pressed by the pressing rolls 33f in a state of being supported by the outer circumferential surface 33c for support in the housing. The pressing rolls 33f are rotated while pressing the guide tube 35 to convey the fluid in the guide tube 35. Reference symbol 33a indicates a manipulation button. The manipulation button 33a is a button configured to turn on and off the pump 33 or to switch between rotational directions of the rotor 33e.

The touch panel 38 more minutely controls the operation of the pump 33 and displays the pumping amount and pumping time of the pump and the internal pressure of the second guide tube portion 35b in real time. The doctor or the nurse may check the operation of the blood collection apparatus 20 with the naked eye through the touch panel 38.

In addition, the operation time of the pump 33 or the rotational speed or the rotational frequency of the rotor may be input in advance through the touch panel 38. Furthermore, when each of the first three-way valve 25 and the second three-way valve 28 is configured to be electronically controlled, each of the first and second three-way valves 25 and 28 may be manipulated through the touch panel 38.

Meanwhile, the check valve 37 is installed between the second port 21e and the pressure accumulation chamber 39, and prevents pressurized air in the pressure accumulation chamber 39 from permeating the saline bag 21 when the fluid in the guide tube 35 moves in the direction indicated by arrow a. The saline solution in the saline bag may move downwards to the guide tube 35 through the check valve 37.

The pressure accumulation chamber is a hermetically sealed container configured to accumulate the pressure of the fluid introduced thereinto as the result of operation of the pump 33. The pressure accumulated in the pressure accumulation chamber 39 serves to push the fluid in the guide tube 35 when the fluid moves in a direction indicated by arrow c as the result of reverse rotation of the pump 33.

Figure 7:
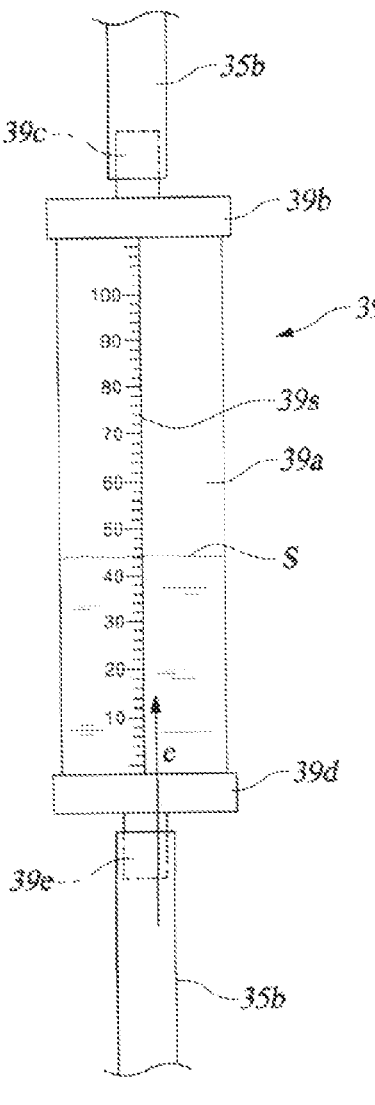
FIG. 7 is a view separately showing a pressure accumulation chamber shown in FIG. 1.

FIG. 7 shows the construction of the pressure accumulation chamber 39.

As shown in FIG. 7, the pressure accumulation chamber 39 has a pressure resistant cylinder 39a, an upper cap 39b, and a lower cap 39d. The pressure resistant cylinder 39a is a cylindrical transparent member that is open at upper and lower parts thereof and that has a scale 39s marked on an outer circumferential surface thereof. The pressure resistant cylinder 39a may be made of acrylic or glass.

The upper cap 39b is a cap configured to close an upper end of the pressure resistant cylinder 39a, and the lower cap 39d is a cap configured to close a lower end of the pressure resistant cylinder. The upper and lower caps 39b and 39d have connection ports 39c and 39e, respectively. The connection ports 39c and 39e are coupled to the second guide tube portion 35b. The saline solution moving downwards from the saline bag 21 passes through the upper cap 39b and is introduced into the pressure resistant cylinder 39a. In addition, the saline solution in the pressure accumulation chamber 39 is discharged downwards through the connection port 39e.

Compressible gas and the saline solution are received in the pressure accumulation chamber 39. The compressible gas may be air. Since the check valve 37 is disposed at an upper part of the pressure accumulation chamber 39, the air is trapped in a space defined between the check valve 37 and a liquid surface of the saline solution S.

Figure 6:
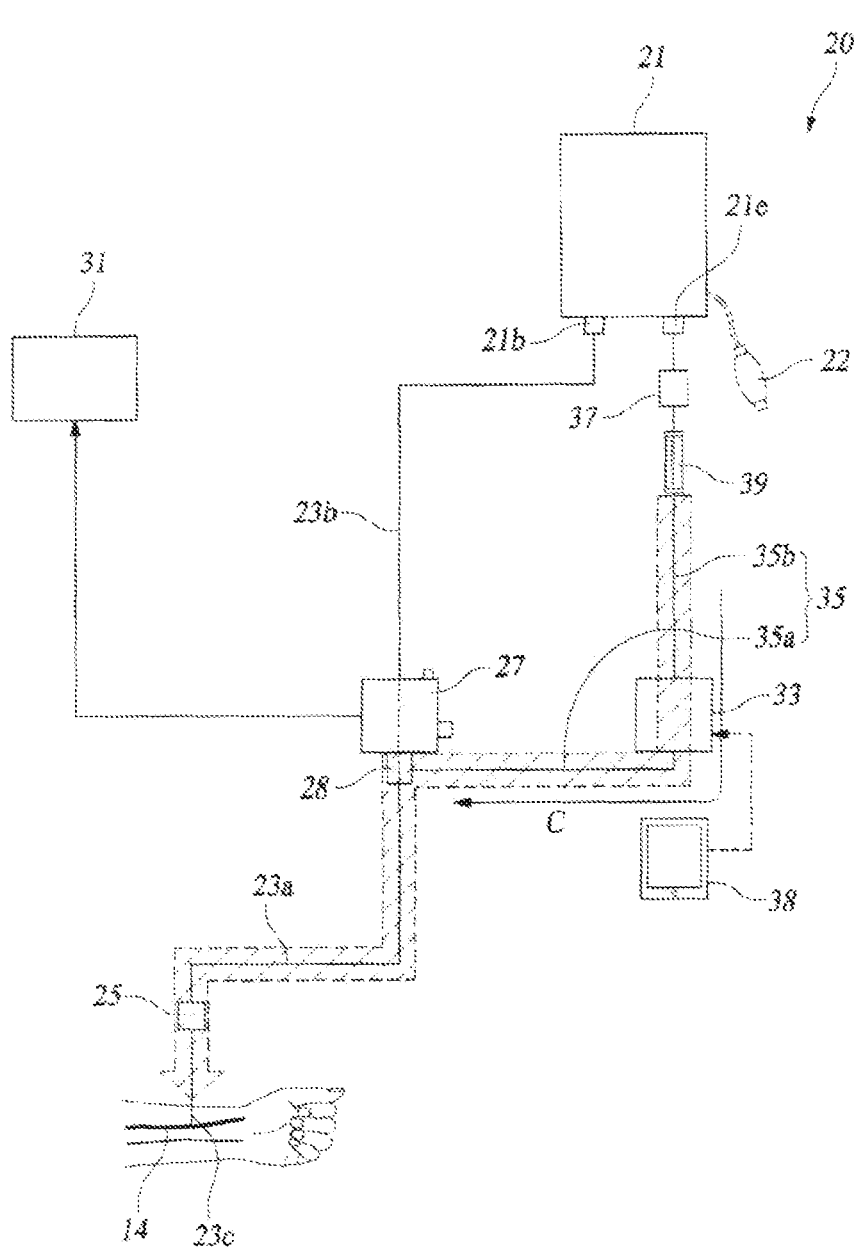

When the fluid in the guide tube 35 is pushed in a direction indicated by arrow e in FIG. 7 as the result of operation of the pump 33, i.e. when the level of the saline solution S increases, air is compressed. When the pump 33 is reversely rotated, the compressed air expands and transmits the force of expansion to the fluid. That is, when fluid in the guide tube 35 moves in the direction indicated by arrow c in FIG. 6, the compressed air pushes the fluid such that the fluid can move more rapidly.

The level of the saline solution in the pressure accumulation chamber 39 may be checked with the naked eye through the scale 39s. When the level of the saline solution increases by 20 ml, the amount of the fluid introduced into the pressure accumulation chamber 39 is 20 ml, which means that 20 ml of blood has been collected from the arterial blood vessel of the patient.

The blood collection apparatus 20 having the above construction is operated as follows.

FIGS. 3 to 6 are views illustrating a method of collecting blood in the artery using the blood collection apparatus 20 of FIG. 1.

Figure 3:
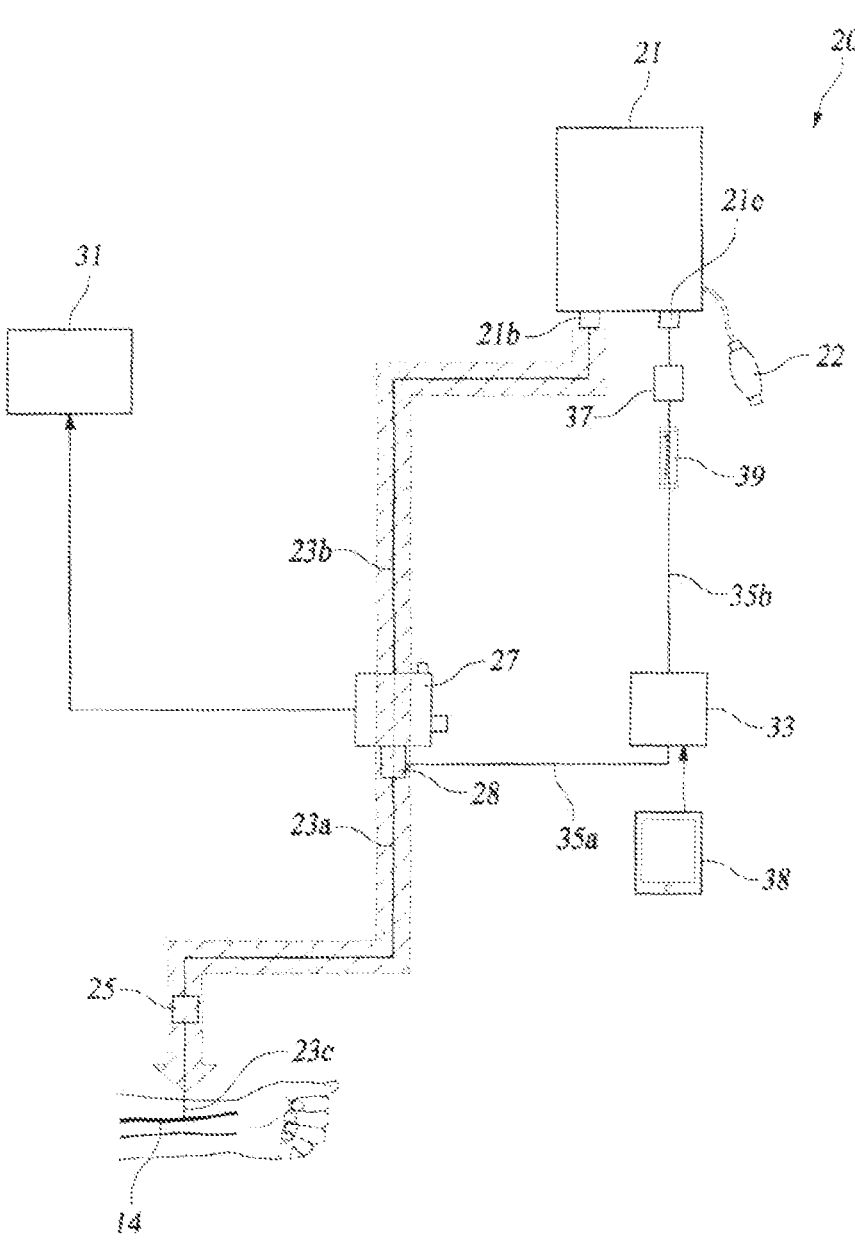
FIGS. 3 to 6 are views illustrating a blood collection method using the blood collection apparatus of FIG. 1.
Figure 4:
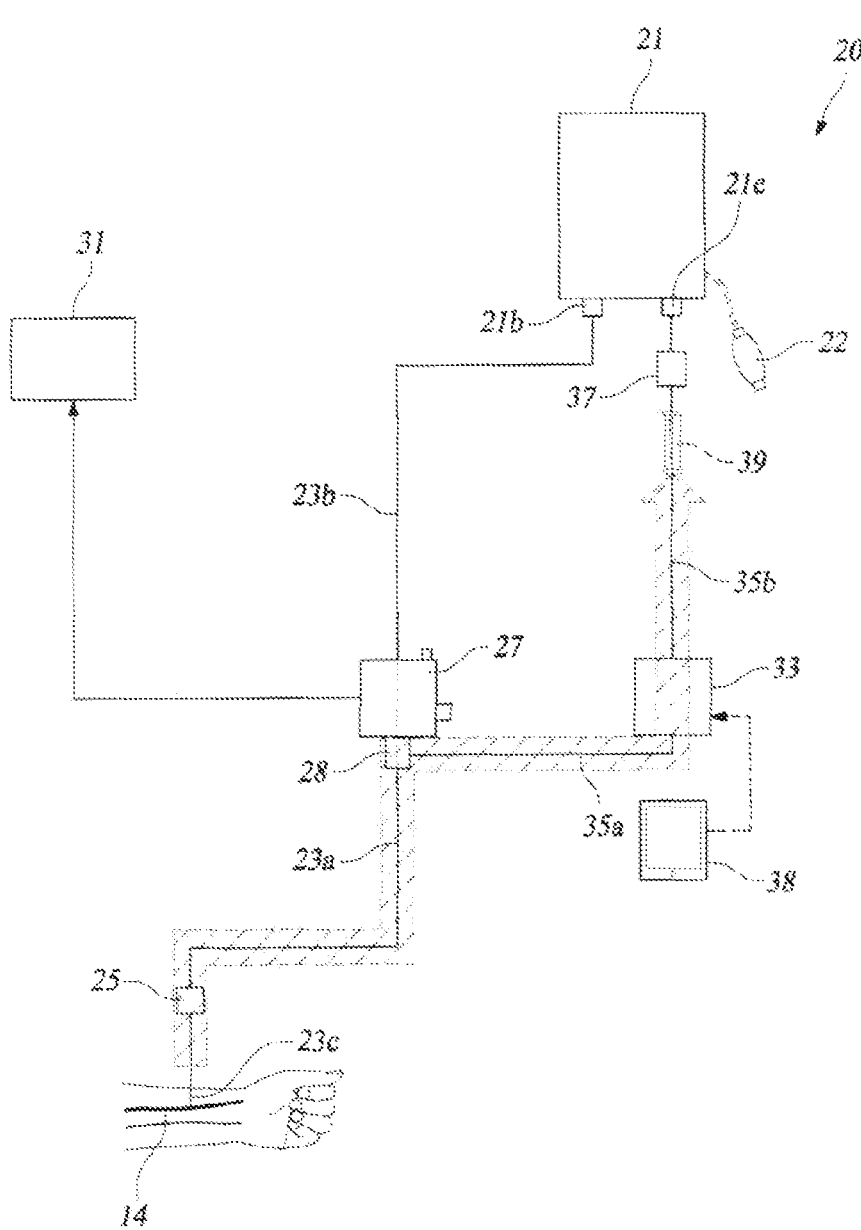

Referring to FIG. 3, the A line 23 is completely open. That is, the catheter 23c and the proximal tube 23a are connected to each other, and the proximal tube 23a and the distal tube 23b are connected to each other. At this time, the interior of the A line 23 is filled with the saline solution including heparin.

In addition, both the internal pressure of the A line 23 and the pressure of the arterial blood vessel are equally adjusted to atmospheric pressure through a separate zeroing process. The pulsation of a heart is transmitted to the transducer 27 through the arterial blood and the saline solution in the proximal tube 23a as media. The transducer 27 converts the pulsation into an electrical signal and transmits the electrical signal to the patient monitor 31.

In order to perform blood collection in the above state, the second three-way valve 28 is operated to allow the proximal tube 23a and the guide tube 35 to communicate with each other. At the same time, the pump 33 is operated to move the saline solution in the proximal tube 23a and the guide tube 35 in the direction indicated by arrow a in FIG. 2.

As the saline solution is conveyed in the direction indicated by arrow a, the blood in the arterial blood vessel 14 is discharged from the arterial blood vessel, moves along with the saline solution, and passes through the first three-way valve 25. The flow rate of the fluid moving in the direction indicated by arrow a is checked through the scale 39s of the pressure accumulation chamber 39. The amount of the blood that is withdrawn may be measured through the scale.

As the above process is performed, initial blood Z1 and internal blood 22 are guided into the proximal tube 23a and the guide tube 35. The internal capacity of each of the proximal tube 23a and the guide tube 35 is fixed. When the amount (ml) of the initial blood is set, therefore, the position of the interface between the initial blood and the internal blood may be easily adjusted by controlling the pump. The interface between the initial blood Z1 and the internal blood Z2 may be located between the first three-way valve 25 and the second three-way valve 28. In addition, the interface between the initial blood Z1 and the saline solution S may be located between the second three-way valve 28 and the pump 33.

When the internal blood Z2 passes through the first three-way valve 25 through the above process, the switching lever 25a of the first three-way valve 25 is turned to open the blood collection port 25e, and the blood collection syringe 41 is inserted into the blood collection port 25e to collect the internal blood.

When collection of the internal blood is completed, the first three-way valve 25 is opened again and the pump 33 is reversely rotated. As the pump is reversely rotated, the residual inner blood, the initial blood, and the saline solution move in the direction indicated arrow c, and the inner blood and the initial blood are transfused into the arterial blood vessel 14. At this time, the compressed air in the pressure accumulation chamber 39 expands and pushes the saline solution.

When the inner blood and the initial blood are introduced into the arterial blood vessel 14, the second three-way valve 28 is manipulated in order to connect the first port 21b and the distal tube 23b to each other and to block the guide tube 35, and the blood collection process is finished.

Figure 8:
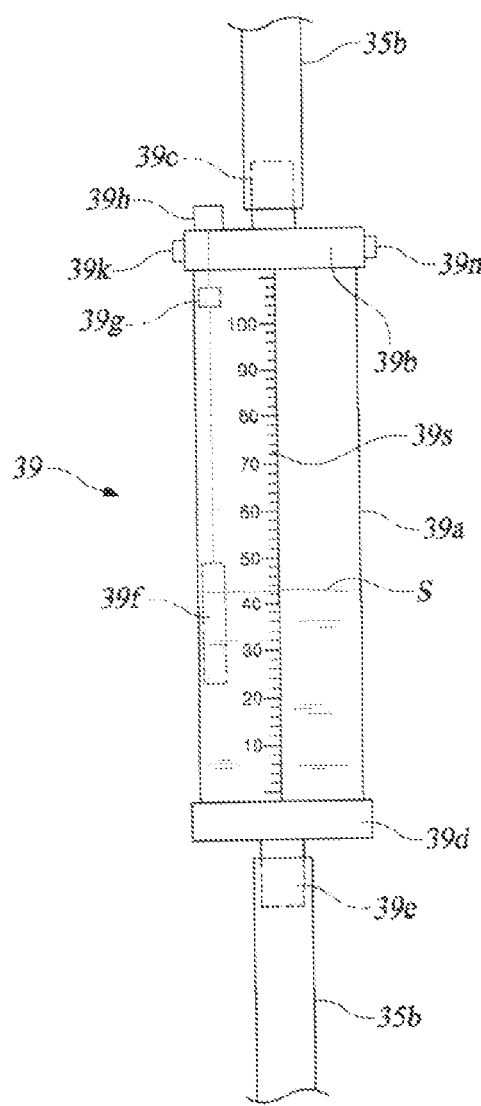
FIG. 8 is a view showing a modification of the pressure accumulation chamber of FIG. 7.

FIG. 8 is a view showing a modification of the pressure accumulation chamber 39 of FIG. 7.

The same reference symbols as the above reference symbols indicate the same members having the same functions.

The pressure accumulation chamber 39 shown in FIG. 8 has a pressure sensor 39g and a water level sensor 39f disposed in a pressure resistant cylinder 39a. The pressure sensor 39g is a sensor configured to sense change in internal pressure of the pressure resistant cylinder 39a, and the water level sensor 39f is a sensor configured to sense change in level of the saline solution S. As the fluid moves in the direction indicated by arrow a in FIG. 2 as the result of operation of the pump 33, as previously described, the level of the saline solution increases and at the same time the internal pressure of the pressure resistant cylinder increases. Change in level and pressure at this time are sensed.

Information sensed by the pressure sensor 39g and the water level sensor 39f is transmitted to a control module 39h. When change in each of the pressure and level in the pressure accumulation chamber 39 exceeds a predetermined range, the control module 39h performs control such that a pressure lamp 39m and a water level lamp 39k are turned on. Each of the pressure lamp 39m and the water level lamp 39k is an LED lamp. The doctor or the nurse who uses the blood collection apparatus 20 may immediately recognize the internal situation of the pressure accumulation chamber 39 through the pressure lamp 39m and the water level lamp 39k without checking the scale 39s.

Figure 9:
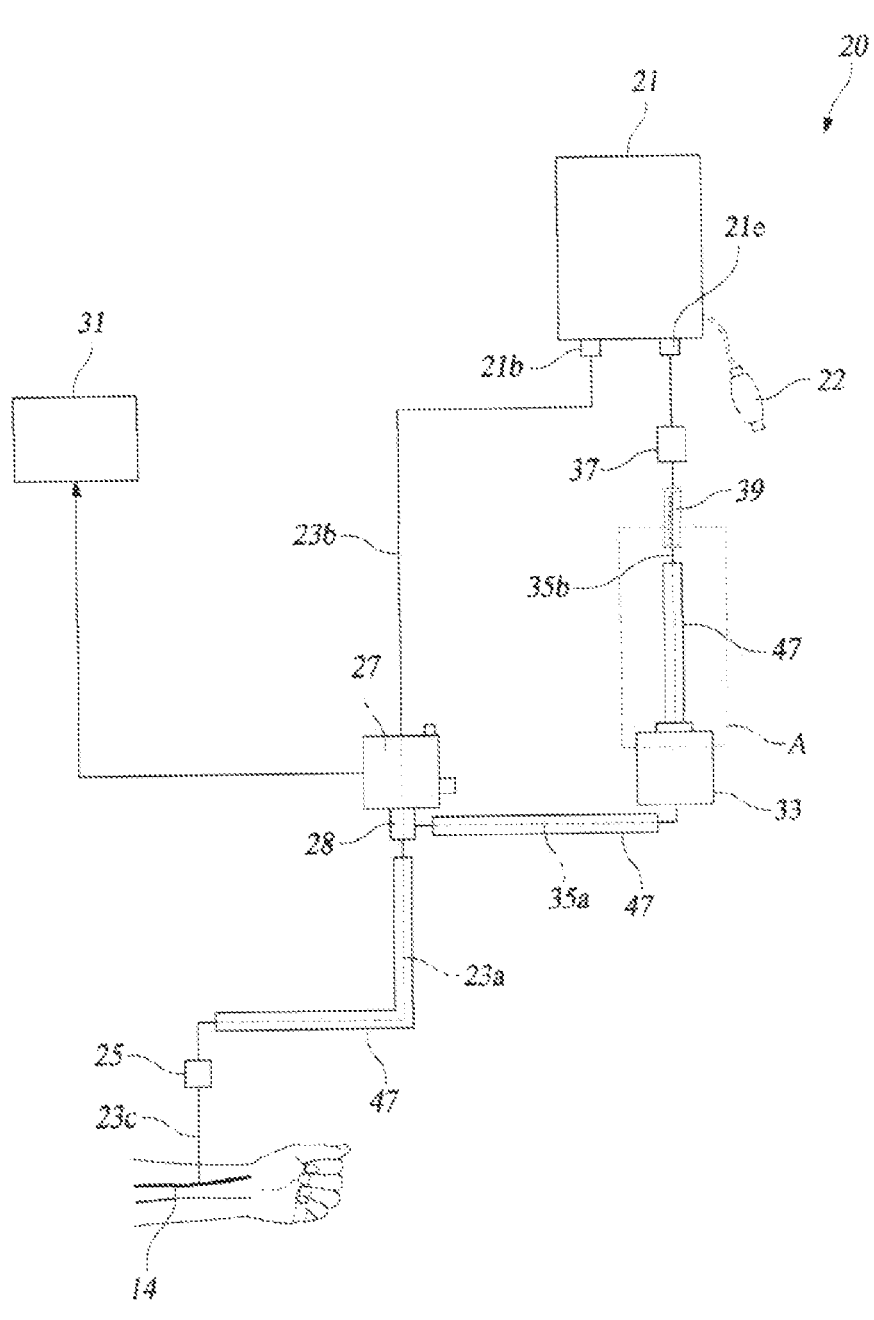
FIG. 9 is a view showing a modification of the closed type arterial blood collection apparatus according to the embodiment of the present invention.
Figure 10:
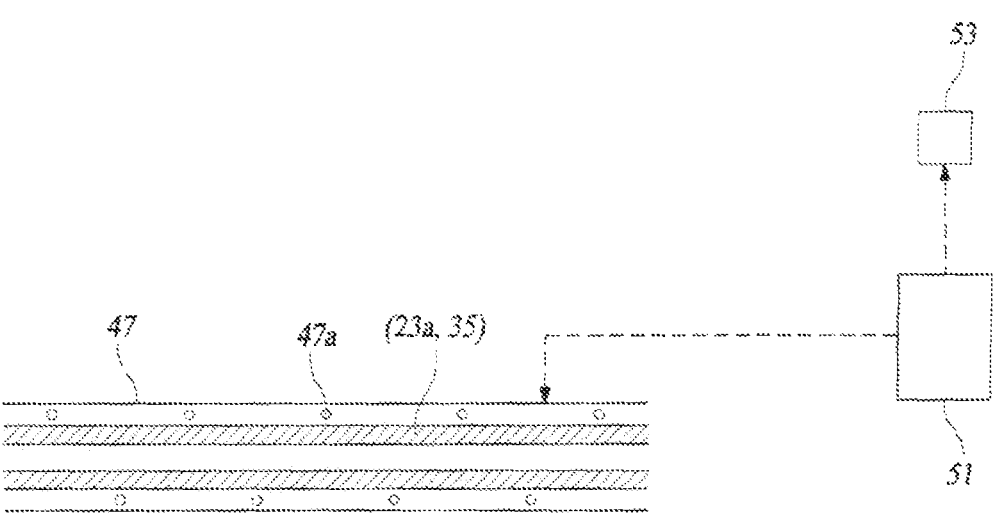
FIG. 10 is a view illustrating a method of operating a constant temperature jacket shown in FIG. 9.

FIG. 9 is a view showing an example in which a constant temperature jacket is applied to the closed type arterial blood collection apparatus 20 according to the embodiment of the present invention, and FIG. 10 is a view illustrating a method of operating the constant temperature jacket shown in FIG. 9.

Referring to the figures, it can be seen that the constant temperature jacket 47 wraps around the proximal tube 23a and the guide tube 35. The constant temperature jacket 47, which is configured to maintain the fluid in the proximal tube 23a and the guide tube 35 at the temperature of the patient, constitutes a temperature maintenance unit together with a temperature controller 51 and an indication lamp 53.

As shown in FIG. 10, the constant temperature jacket 47 has a heating wire 47a mounted therein. The heating wire 47a generates heat using electricity transmitted from the temperature controller 51 to maintain the constant temperature jacket 47 at a predetermined temperature. The temperature controller 51 controls the temperature of the constant temperature jacket 47.

In addition, the indication lamp 53 is an LED lamp configured to be turned on when the temperature of heat generated by the constant temperature jacket 47 is within a normal range. It can be seen with the naked eye through the indication lamp 53 that the temperature in the fluid in the second guide tube portion 35b is maintained at the temperature of the patient. When the temperature maintenance unit is provided, as described above, it is possible to maximally inhibit the formation of thrombi. The temperature of the constant temperature jacket 47 may be set to be higher or lower than the temperature of the patient, as needed. In addition, the installation position of the constant temperature jacket 47 may be freely changed.

Although the present invention has been described in detail with reference to the specific embodiments, the present invention is not limited to the embodiments and may be variously modified by a person having ordinary skill in the art without departing from the technical idea of the present invention.

The invention claimed is:

1. A closed type arterial blood collection apparatus comprising:

a saline bag configured to receive a saline solution, wherein a first port and a second port are provided at a lower end of the saline bag;

an A line configured to connect an arterial blood vessel of a patient to the first port, the A line being filled with the saline solution from the saline bag;

a first three-way valve configured to open and close the A line in a state of being mounted on the A line;

a blood collection syringe configured to collect arterial blood through the first three-way valve when the first three-way valve closes the A line;

a second three-way valve provided between the first three-way valve and the first port, the second three-way valve being configured to open and close the A line;

a guide tube configured to connect the second three-way valve to the second port, the guide tube being filled with the saline solution from the saline bag; and a fluid conveying unit configured to convey a fluid in the guide tube to the saline bag when the A line and the guide tube are connected to each other as a result of operation of the second three-way valve, wherein the A line comprises a catheter having a blood collection needle, the catheter being connected to the first three-way valve, a proximal tube configured to connect the first three-way valve and the second three-way valve to each other, and a distal tube configured to connect the second three-way valve and the first port to each other, the A line is configured to directly connect the saline bag and the arterial blood vessel to each other in a state of bypassing the guide tube through the second three-way valve, to receive the saline solution from the saline bag, and to transmit a pulse signal of an artery of the patient through the saline solution, a transducer configured to be mounted on the A line and convert the pulse signal of the artery of the patient transmitted through the saline solution used as a medium into an electrical signal and to transmit the electrical signal to an external patient monitor, the blood collection syringe collects the arterial blood of the patient through the proximal tube in a state in which the distal tube between the first port and the guide tube is closed through the second three-way valve, the proximal tube and the guide tube communicate with each other through the second three-way valve, and the arterial blood is moved along with the saline solution from the arterial blood vessel to the guide tube, and the fluid conveying unit comprises a pump configured to press an outer circumferential surface of the guide tube in a longitudinal direction thereof in order to push and thus move the arterial blood in the guide tube in the longitudinal direction of the guide tube such that an interface between initial blood and internal blood is located between the first three-way valve and the second three-way valve and an interface between the initial blood and the saline solution is located between the second three-way valve and the fluid conveying unit in a state in which the distal tube between the first port and the guide tube is closed through the second three-way valve and the proximal tube and the guide tube communicate with each other through the second three-way valve.

2. The closed type arterial blood collection apparatus according to claim 1, wherein a check valve configured to prevent the fluid introduced into the guide tube from the proximal tube via the second three-way valve from being introduced into the second port is installed between the pump and the second port.

3. The closed type arterial blood collection apparatus according to claim 2, wherein a pressure accumulation chamber configured to accumulate inner pressure of the guide tube increasing as a result of operation of the pump is further installed between the pump and the check valve, wherein the pressure accumulation chamber has a pressure resistant cylinder configured to receive compressible gas and the saline solution, and wherein the pressure resistant cylinder has a scale for indicating a level of the saline solution inside of the pressure resistant cylinder, the scale being marked on a surface of the pressure resistant cylinder, the level of the saline solution being changed based on a change in an inner pressure of the pressure resistant cylinder.

4. The closed type arterial blood collection apparatus according to claim 3, wherein the pressure accumulation chamber further has:

a pressure sensor configured to sense the inner pressure of the pressure resistant cylinder;

a water level sensor configured to sense the level of the saline solution;

a control module connected to the pressure sensor and the water level sensor, the control module being configured to output a signal when change in each of the inner pressure of the pressure resistant cylinder and the level of the saline solution exceeds a predetermined range; and a pressure lamp and a water level lamp configured to be operated under control of the control module.

5. The closed type arterial blood collection apparatus according to claim 1, wherein a temperature maintenance unit configured to maintain a temperature of the fluid in the A line or the guide tube at a temperature of the patient is installed, wherein the temperature maintenance unit comprises:

a constant temperature jacket configured to wrap around the A line or the guide tube;

a temperature controller configured to control a temperature of the constant temperature jacket; and an indication lamp configured to be turned on when a temperature of heat generated by the constant temperature jacket is within a normal range.

* * * * *